United States Patent [19]

Salkin

[11] Patent Number: 4,814,334

[45] Date of Patent: Mar. 21, 1989

[54] COMPOSITION WITH HIGH BACTERICIDAL POWER CONTAINING A BIGUANIDE AND A PYRIMIDINE

[76] Inventor: Andre Salkin, 134, avenue du 14 Juillet, 76300 Sotteville les Rouen, France

[21] Appl. No.: 848,456

[22] Filed: Apr. 4, 1986

Related U.S. Application Data

[63] Continuation of Ser. No. 651,804, Sep. 18, 1984, abandoned.

[30] Foreign Application Priority Data

Sep. 22, 1983 [FR] France ................. 83 15100

[51] Int. Cl.$^4$ .................. A01N 43/54; A01N 37/52; A61K 31/505; A61K 31/155
[52] U.S. Cl. ................................. 514/256; 514/635
[58] Field of Search ................. 514/256, 635

[56] References Cited

U.S. PATENT DOCUMENTS 3,957,967 5/1976 L'Orange ................. 424/48

FOREIGN PATENT DOCUMENTS 7121 9/1969 France .

OTHER PUBLICATIONS

The Merck Index; 9th Ed. (1976) #2060; "Chlorhexidine" p. 265.

*Primary Examiner*—Leonard Schenkman
*Assistant Examiner*—Joseph A. Lipovsky

[57] ABSTRACT

The invention relates to compositions having a high bactericidal power, wherein they contain:
at least one derivative of biguanide selected from hexamethylene-bis-5-(p-chlorophenyl)-biguanide (chlorhexidine) and the hydrochloride of polyhexamethylenebiguanide (PHMB),
and, 1,3-bis-($\beta$-ethylhexyl)-5-aminohexahydropyrimidine (hexetidine).

12 Claims, No Drawings

COMPOSITION WITH HIGH BACTERICIDAL POWER CONTAINING A BIGUANIDE AND A PYRIMIDINE

This application is a continuation of application Ser. No. 651,804 filed Sept. 18, 1984 now abandoned.

The present invention relates to novel compositions having a high bactericidal power.

Numerous products having a high bactericidal power are known. Each of such products presents a certain spectrum of activity against the various species against which it may be used. However, it may be advantageous to have products available which possess, on the one hand, a spectrum of activity which is as complete as possible, and, on the other hand, with respect to certain species, a more pronounced bactericidal power. This may be obtained by making mixtures of several bactericides, but the known bactericides used in these mixtures must be compatible with one another, complementary, and must provoke the desired effects of synergy. That is the object of the present invention.

The invention therefore relates to compositions having a high bactericidal power comprising known bactericidal products which are, on the one hand, at least one derivative of biguanide selected from hexamethylene-bis-5-(p-chlorophenyl)-biguanide (chlorohexidine) and the hydrochloride of polyhexamethylenebiguanide (PHMB), and, on the other hand, 1,3-bis-$\beta$-ethylhexyl)-5-aminohexahydropyrimidine (hexetidine).

The biguanides selected are known for their germicidal power against gram + and gram − germs, for their absence of toxicity and of phenomena of irritation upon contact with the skin and mucous membranes. However, both have shortcomings, particularly a low anti-fungal power and a certain instability to light and to pH variations and to the presence of surface-active products. The PHMB is the more stable, but its fungicidal action is also very weak.

It has been attempted to overcome the lack of fungicidal power of these biguanides by making compositions containing, in addition to said biguanides. a quarternary ammonium compound. In certain cases, interesting results have been obtained, but the high toxicity of the quaternary ammonium compounds, which are all sensitizing and irritating and, moreover, very sensitive to the presence of proteins such as blood, pus, milk, etc . . . , must be taken into account.

The second compound (hexetidine) is used as a cicatrizing disinfectant antiseptic for the mouth and all the natural cavities in human beings.

According to the Vidal pharmaceutical dictionary, hexetidine is non-toxic; in fact no LD 50 was determined at massive doses in animal trials.

The antibacterial power of hexetidine is due to the interference with the vital metabolic process necessary for the growth of the pathogenic microorganisms.

The anti-microbial and antifungic properties are accentuated by the particular affinity of hexetidine with the proteins of the skin and the mucous membranes—a very important factor of its disinfecting efficacy since it disappears only very slowly from the surfaces having been treated.

Hexetidine is known as being more active against the gram + bacteria (where it is effective at very low doses), including BK (tuberculosis), than against the gram − bacteria where higher concentrations are necessary.

In the compositions according to the invention, from 0.01 to 1 part by weight of at least one biguanide is used for 0.0025 to 0.15 parts by weight of hexetidine.

The mixtures according to the invention present certain effects of synergy; for example, these mixtures effectively fight against certain gram − bacteria such as *Pseudomonas aeruginosa*, responsible to a large extent for superinfection in hospitals. In practice, it may be shown that said mixtures (particularly the solutions which contain about 0.5% of chlorhexidine and about 0.1% of hexetidine) kill most of the colonies of gram + and gram − bacteria, yeasts and fungi, in less than a minute.

However, in addition, the very important effect of remanance obtained with the mixtures according to the invention will be noted. This effect is probably due to the presence and to the mode of action of the hexetidine in the mixture. When the skin, a wound, a burn, are left in the open air and are rinsed, the local concentration of the biguanide derivatives may be considerably reduced and yet it appears that, thanks to the presence of hexetidine, the remaining biguanide derivative will continue to have a pronounced bacteriostatic action.

The compositions according to the invention may be used in various forms, such as for example solutions, emulsions, gels, ointments, . . . . The preferred form is a solution in a compatible solvent, this compatibility having to be assessed on the one hand with respect to the active products themselves (biguanide and hexetidine) and, on the other hand, to the use envisaged (innocuousness) with respect to the skin for example).

The soluble compositions according to the invention will therefore comprise from 0.01 to 1% by weight of at least one selected biguanide and from 15 ppm to 0.5% by weight of hexetidine.

The compositions according to the invention may be used whenever it is desired to have available a product with high bactericidal and fungicidal power. The following applications may be envisaged:

disinfection of the hands of hospital staff;
disinfection of objects such as feeding bottles, dentures, brushes, . . .
disinfection of equipment and skin in the veterinary field;
hygiene, care and treatment of skins suffering from acne.

When surgeons wash their hands before putting on gloves and when nurses rinse their hands with a quick-drying water-alcohol solution, the phenomenon of remanence will appear and will protect both the patient and the hospital staff for several hours.

The synergetic phenomenon enables lower concentrations to be used than that provided for the products applied separately. This may be very important in certain cases. However, the mixtures according to the invention will, in any case, enable greater security to be obtained.

When the mixtures according to the invention are in the form of solutions, the solvent used may either be water or alcohol or water and alcohol mixtures; however, the other admissible solvents may also be used.

Furthermore, it will be noted that if, during use, the solutions according to the invention must contain only fairly small proportions of active products, it is quite possible and even often desirable to market mother solutions with a much greater concentration of active products.

The following non-limiting examples illustrate the invention.

For the purposes of subsequent comparison, the results obtained with the various elements of the combination when employed separately and certain combinations according to the invention will firstly be mentioned hereinafter.

For these results:

column A represents the minimum concentration (in ppm) for inhibiting growth of the species in question, the results are given in ppm of active principle;

column B represents the quantity (in ppm) of active principle necessary for complete destruction (100%) of the species.

The following results were obtained:

| Product tested | A | B |
|---|---|---|
| *Staphylococcus aureus* | | |
| PHMB 20% solution | 20 | 1000 |
| Chlorhexidine 20% solution | 5–10 | 600 |
| Hexitidine | 10 | 200 |
| Mixture according to invention | | |
| 0.5% of biguanide / 0.2% of hexetidine | 0.5 | 40 |
| *Candida albicans* | | |
| PHMB 20% solution | 250 | 2500 |
| Chlorhexidine 20% solution | 35–75 | — |
| Hexetidine | 60 | 75 |
| Mixture of invention | | |
| 0.5% of biguanide / 0.2% of hexetidine | 10–15 | 75 |
| *Escherichia coli* | | |
| PHMB 20% solution | 20 | 500 |
| Chlorhexidine 20% solution | 5–25 | >800 |
| Hexetidine | 100 | >1000 |
| Mixture according to invention | | |
| 0.5% of biguanide / 0.2% of hexetidine | 3–5 | 62.5 |
| *Pseudomonas aeruginosa* | | |
| PHMB 20% solution | 100 | 2500 |
| Chlorhexidine 20% solution | 15–300 | 2500 |
| Hexetidine | 100–300 | 1000 |
| Mixture according to invention | | |
| 0.5% of biguanide / 0.2% of hexetidine | 10 | 75–125 |

The mixtures described hereinafter were used for various applications.

EXAMPLES 1 TO 4

(1) Solutions for general disinfection

| | | |
|---|---|---|
| PHMB 100% | 0.05 to 0.5% | |
| Chlorhexidine 100% | | 0.05 to 0.5% |
| Hexetidine | 0.05–0.15% | 0.05–0.15% |
| Organic sequestrum-producer | 0.05 to 1% | 0.05–1% |
| Wetting agent | 0.05 to 0.15% | 0.05 to 0.15% |
| Iso alcohol/water (60%) | qsp | qsp |

(2) Solutions for disinfecting surgeon's hands

| | | |
|---|---|---|
| PHMB | 0.25–1% | |
| Chlorhexidine | — | 0.25–1% |
| Hexetidine | 0.1–0.15% | 0.1–0.15% |
| Organic sequestrum-producer | 0.5–1% | 0.5–1% |
| Betain (30%) | 20–25% | 20–25% |
| Ethoxylated fatty alcohol (or octylcresylethoxylated alcohol) | 4–5% | 4–5% |
| Iso alcohol/water (60%) | qsp | qsp |

(3) Solution used for disinfecting instruments

| | |
|---|---|
| Biguanide derivatives | 1% |
| Hexetidine | 0.25% |
| Surface-active agent | 0.1% |
| Organic sequestrum-producer | 0.5 to 1.5% |
| pH | 6 to 7 |
| Iso alcohol/water (60%) | qsp |

(4) Other solution used for instruments

| | |
|---|---|
| Biguanide derivatives | 1 to 1.5% |
| Hexetidine | 0.15 to 0.3% |
| Glutaraldehyde (50%) | 1 to 2% |
| Sequestrum-producer DETP | 0.75% |
| Iso alcohol/water (60%) | qsp |
| pH | 6 |

EXAMPLE 5

An example of a concentrated solution containing the active products and capable of producing the solutions according to the invention is given hereinafter:

| | |
|---|---|
| PHMB or chlo rhexidine (20%) | 20% |
| Hexetidine | 4% |
| Ethoxylated fatty alcohol | 5% |
| Iso alcohol (or ethanol) | 24% |
| Organic sequestrum-producer (40% solution) | 10% |
| pH buffer 6.5 | |
| Iso alcohol/water (60%) | qsp |

Such a solution may advantageously be diluted 20 to 50 times.

EXAMPLE 6

Aqueous solutions, containing no alcohol, of hexetidine and biguanide are prepared; these solutions may be obtained:

either by using a surface-active agent such as sorbitol monolaurate; the following solutions have been prepared this way:

| | |
|---|---|
| (A) Chlorhexidine | 0.5% |
| hexetidine | 0.2% |
| sorbitol monolaurate | 2.8% |
| water | s.q.f. (100 g) |
| the pH of the solution being 6 to 6.5 | |
| (B) PHMB | 0.5% |
| hexetidine | 0.2% |
| sorbitol monolaurate | 2% |
| water | s.q.f. (100 g) | or by using hexetidine in the form of its trihydrochloride.

What is claimed is:

1. A bactericidal composition consisting essentially of (a) about 0.01 to 1 percent by weight of at least one derivative of biguanide selected from the group consisting of: hexamethylene-bis-5-(p-chlorophenyl)-biguanide and the hydrochloride of polyhexamethylenebiguanide, (b) about 0.0025 to 0.3 percent by weight of 1,3-bis-($\beta$-ethylhexyl)-5-aminohexahydropyrimidine, (c) about 0.05 to 1.5 percent by weight of organic sequestering agent, and (d) about 0 to 2 percent by weight of glutaraldehyde.

2. A method of disinfecting a surface comprising the step of contacting the surface with a disinfecting effective amount of a bactericidal composition according to claim 1.

3. A method of treating acne comprising the step of applying to the affected area an acne-treating effective amount of a bactericidal composition according to claim 1.

4. A bactericidal composition consisting essentially of:

(a) about 0.01 to 1 percent by weight of at least one biguanide selected from hexamethylene-bis-(p-chlorophenyl)-biguanide and the hydrochloride of polyhexamethylene-biguanide, and (b) about 0.0025 to 0.3 percent by weight of 1,3-bis-($\beta$-ethylhexyl)-5-aminohexahydropyrimidine.

5. A bactericidal composition according to claim 4 which includes at least one of an organic sequestering agent, a surface active agent and glutaraldehyde.

6. A bactericidal composition according to claim 4 which is a solution in which the solvent is selected from ethanol and water, and mixtures thereof.

7. A method for destroying bacteria which comprises the step of applying a disinfecting amount of the solution of claim 6 to said bacteria.

8. A bactericidal solution according to claim 6 in which said solvent is a mixture of ethanol and water, optionally with a surface active agent.

9. A method for destroying bacteria which comprises the step of applying a disinfecting amount of the solution of claim 8 to said bacteria.

10. A method for destroying bacteria which comprises the step of applying a disinfecting amount of the composition of claim 4, to said bacteria.

11. A bactericidal concentrate which upon dilution by a factor of 20 to 50 times consists essentially of:

(A) About 0.01 to 1 percent by weight of at least one derivative of biguanide selected from the group consisting of
hexamethylene-bis-5-(p-chlorophenyl)-biguanide and the hydrochloride of polyhexamethylenebiguanide, (B) About 0.0025 to 0.3 percent by weight of 1,3-bis-(beta-ethylhexyl)-5-aminohexahydropyrimidine, (C) About 0.05 to 1.5 percent by weight of organic sequestering agent, and (D) About 0 to 2 percent by weight of glutaraldehyde.

12. A bactericidal concentrate which upon dilution by a factor of 20 to 50 times consists essentially of:

(A) About 0.01 to 1 percent by weight of at least one biguanide selected from the group consisting of hexamethylene-bis-(p-chlorophenyl)-biguanide and the hydrochloride of polyhexamethylenebiguanide, and (B) About 0.0025 to 0.3 percent by weight of 1,3-bis-(beta-ethylhexyl)-5-aminohexahydropyrimidine.

* * * * *